（12）United States Patent
Marshall et al.

(10) Patent No.: US 7,298,876 B1
(45) Date of Patent: Nov. 20, 2007

(54) METHOD AND APPARATUS FOR QUALITY ASSURANCE AND QUALITY CONTROL IN RADIOLOGICAL EQUIPMENT USING AUTOMATIC ANALYSIS TOOLS

(75) Inventors: Julian Marshall, Los Altos, CA (US); Keith W. Hartman, Redwood City, CA (US)

(73) Assignee: R2 Technology, Inc., Santa Clara, CA (US)

( * ) Notice: Subject to any disclaimer, the term of this patent is extended or adjusted under 35 U.S.C. 154(b) by 630 days.

(21) Appl. No.: 10/288,151

(22) Filed: Nov. 4, 2002

(51) Int. Cl.
*G06K 9/00* (2006.01)
*A61B 6/00* (2006.01)
*H05G 1/02* (2006.01)
*G01T 1/161* (2006.01)
*G01T 3/00* (2006.01)

(52) U.S. Cl. .................. 382/128; 378/20; 378/195; 250/363.02; 250/390.02; 250/390.12

(58) Field of Classification Search ........ 382/128–132; 250/252.1, 256, 362, 363.01–363.05, 370.08–370.11, 250/390.02, 390.06, 390.12; 378/20, 45–46, 378/48, 87, 193–198, 204–209
See application file for complete search history.

(56) References Cited

U.S. PATENT DOCUMENTS 2,426,884 A * 9/1947 Kieffer ............... 378/207
4,057,727 A * 11/1977 Muehllehner et al. . 250/363.03
4,543,959 A * 10/1985 Sepponen .............. 600/440

(Continued)

FOREIGN PATENT DOCUMENTS

WO    WO 98/52011 A2    11/1998

OTHER PUBLICATIONS

Nassivera, E., and Nardin, L., "Quality Programme in Mammography: Second Level Quality Control" The British Journal of Radiology, Jun. 1997, pp. 612-618.*

(Continued)

*Primary Examiner*—Bhavesh M Mehta
*Assistant Examiner*—Manav Seth
(74) *Attorney, Agent, or Firm*—Blakely, Sokoloff, Taylor & Zafman, LLP; Judith A. Szepesi

(57) ABSTRACT

A method and apparatus for providing testing a computer aided diagnosis (CAD)-based system comprising receiving radiological image of a patient acquired using at least one piece of radiological equipment at least partially controlled by a technologist, the patient being controlled by the technologies relative to the radiological equipment in acquiring said radiological image. The method further comprising processing the radiological image by computer to test the radiological image to determine if the image meets a preselected standard relating to at least one of: technologist control of the patient relative to the radiological equipment during the image acquisition and technologist preparation of the radiological equipment for the image acquisition, wherein said preselected standard relating to technologist control of the patient relative to the radiological equipment during the image acquisition relates to one of (a) proper placement of anatomical part of the patient relative to a detector of the radiological equipment, and (b) controlling movement of the anatomical part of the patient relative to the detector during image acquisition. The method further comprising recording the results of the testing in a manner that associates said results with said technologist for facilitating evaluation of a performance of said technologist.

12 Claims, 10 Drawing Sheets

U.S. PATENT DOCUMENTS

| | | | | |
|---|---|---|---|---|
| 4,550,422 | A * | 10/1985 | VanPelt et al. | 378/207 |
| 4,887,286 | A * | 12/1989 | Seidenberg | 378/170 |
| 5,124,913 | A * | 6/1992 | Sezan et al. | 382/132 |
| 5,165,410 | A * | 11/1992 | Warne et al. | 378/206 |
| 5,270,530 | A * | 12/1993 | Godlewski et al. | 250/208.1 |
| 5,406,612 | A * | 4/1995 | Galkin | 378/207 |
| 5,565,678 | A * | 10/1996 | Manian | 250/252.1 |
| 5,600,574 | A * | 2/1997 | Reitan | 702/185 |
| 5,717,735 | A * | 2/1998 | Ramsdell et al. | 378/208 |
| 5,786,994 | A * | 7/1998 | Friz et al. | 700/79 |
| 5,793,969 | A * | 8/1998 | Kamentsky et al. | 709/213 |
| 5,854,850 | A * | 12/1998 | Linford et al. | 382/128 |
| 5,875,258 | A * | 2/1999 | Ortyn et al. | 382/133 |
| 5,917,929 | A * | 6/1999 | Marshall et al. | 382/128 |
| 6,258,605 | B1 * | 7/2001 | Chace | 436/86 |
| 6,370,480 | B1 * | 4/2002 | Gupta et al. | 702/39 |
| 6,401,055 | B1 * | 6/2002 | Petta | 702/182 |
| 6,409,383 | B1 * | 6/2002 | Wang et al. | 378/207 |
| 6,626,569 | B2 * | 9/2003 | Reinstein et al. | 378/206 |
| 6,669,482 | B1 * | 12/2003 | Shile | 434/262 |
| 6,760,402 | B2 * | 7/2004 | Ghelmansarai | 378/65 |
| 6,911,988 | B1 * | 6/2005 | Tsujii | 378/206 |
| 6,934,590 | B2 * | 8/2005 | Ogawa | 700/19 |
| 6,937,751 | B2 * | 8/2005 | Ritt et al. | 382/132 |
| 2002/0194019 | A1 * | 12/2002 | Evertsz | 705/2 |
| 2003/0007675 | A1 * | 1/2003 | Schmidt et al. | 382/132 |
| 2003/0153991 | A1 * | 8/2003 | Visser et al. | 700/79 |
| 2004/0156472 | A1 * | 8/2004 | Galkin | 378/37 |
| 2006/0056670 | A1 * | 3/2006 | Hamadeh | 382/128 |

OTHER PUBLICATIONS

Costa, P. et al. "Development of a Real-Time Management System for Quality Assurance Programmes in Imaging Diagnostics Departments." Proc. of 22nd Annual EMBS International Conf., Jul. 23-28, 2000, pp. 2522-2525.*

* cited by examiner

| QA | QC |
|---|---|
| (Periodic Testing) | (Continuous Testing) |
| Testing for Presence of: | Testing for: |
| Phantom images | Positioning |
| Fog | Procedure |
| dirt on screen | Absence of Motion Blur |
| | Adequate Compression (mammo) |
| | Appropriate Dosage |
| | Sufficient Penetration |
| | Correct Marker Positioning |
| | Flash exposure |
| | Contrast |
| | Dynamic Range |
| | Hardware Image Artifacts |

Fig. 7

METHOD AND APPARATUS FOR QUALITY ASSURANCE AND QUALITY CONTROL IN RADIOLOGICAL EQUIPMENT USING AUTOMATIC ANALYSIS TOOLS

FIELD OF THE INVENTION

The present invention relates to radiological systems, and more specifically, to quality assurance and quality control in radiological systems.

BACKGROUND

Radiological systems are used for X-rays, mammograms, MRIs, and similar procedures. In general, quality assurance and quality control tests are mandated. For example, for mammograms, there are a series of quality control tests, which are carried out daily, weekly, and monthly. These tests generally require the imaging technician to take a sample image, and analyze it for various error indications. For example, images may be analyzed to determine whether there are phantom images, fog, development errors, etc. Similarly, specific tests for the particular type of device may be made as well. For example, for mammograms a compression test and screen-film contact tests may be carried out.

In the prior art, these tests are carried out manually. The technician takes one or more images, using standard procedures, and then either the technician or a radiologist analyses the image(s) to determine whether there are any problems. In general, these results are then charted on a "processing control chart" or similar chart. These results are used to review the equipment as well as the technician, and to potentially adjust the equipment, or instruct the technician in the correct procedures to produce better quality images.

SUMMARY OF THE INVENTION

A method and apparatus for using a computer-aided diagnosis system for quality evaluation of radiological equipment.

BRIEF DESCRIPTION OF THE DRAWINGS

The present invention is illustrated by way of example, and not by way of limitation, in the figures of the accompanying drawings and in which like reference numerals refer to similar elements and in which:

FIG. 7 is a table showing a comparison between QA and QC testing.

DETAILED DESCRIPTION

The present invention is a method and apparatus for using a computer-aided diagnosis system for quality evaluation of radiological equipment. A computer-aided diagnosis (CAD) system is designed to assist a radiologist in analyzing radiological images, such as mammograms, chest X-rays, MRIs, and similar radiological images. U.S. Pat. No. 6,014,452 describes one exemplary CAD system that may be used with the present invention. However, any CAD system may be used. The CAD systems all analyze images for unexpected elements. This methodology can be used for quality assurance (QA) and quality control (QC). The QA and QC processes together will be referred to as quality evaluation.

For one embodiment, the system is initially provided with the "clean" or ideal set of images. Subsequent images are compared to that set. For another embodiment, the system is provided with a large initial set of images. These images form a "basis" for evaluating subsequent images. The quality evaluation is whether the subsequent images match this basis set. For another embodiment, each image that is evaluated using the standard CAD procedures is further evaluated for QC and QA problems. If such a problem is found, it is automatically brought to the attention of the technician.

For one embodiment, the results are charted, and stored in a database. These results are then made available to the technician, as well as to others, for review.

Figure 1:
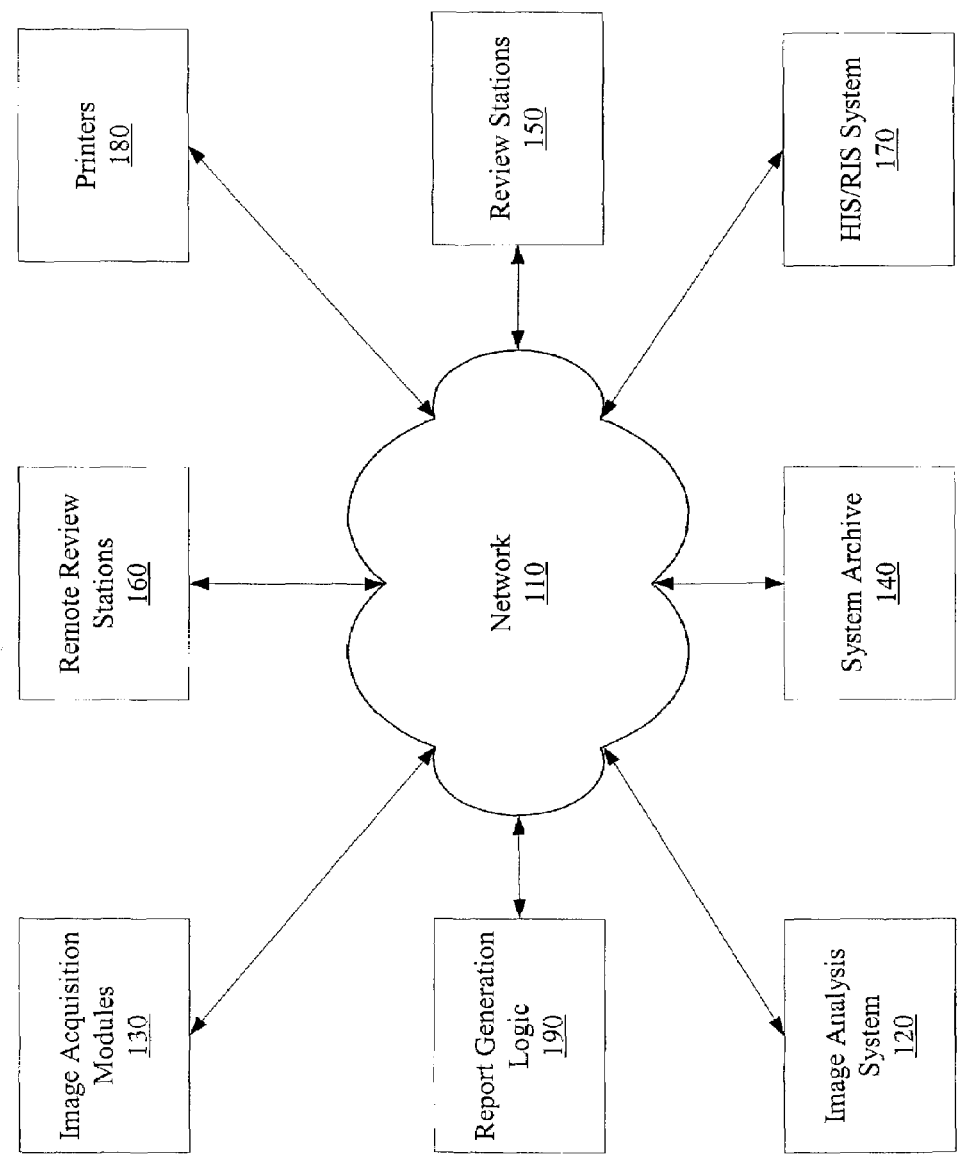
FIG. 1 is a block diagram of a network with which the present system may be used.

FIG. 1 is a block diagram of a network that may be used with the present invention. The system includes one or more image acquisition modules 130A, 130B. The image acquisition modules 130A, 130B may be conventional medical image acquisition systems, which are known in the art, and/or digital image acquisition systems. Standard methods—such as mammogram films, CAT scans, chest X-rays, or others—may be used to obtain the analog or digital images, whether two or three-dimensional. The outputs of the image acquisition modules 130A, 130B, are digital or analog images.

These images are passed to image analysis system 120. For one embodiment, the images are sent through network 110 to image analysis system 120. Network 110 may be an internal local area network (LAN), a wide area network (WAN), the Internet, or any other type of network. For one embodiment, if the network 110 is not a local internal network, then the images sent by image acquisition modules 130A, 130B are encrypted or in some other way protected to ensure the patient's privacy. This permits the use of a centralized image analysis system 120 which may receive images from multiple offices that may be located anywhere in the world. Similarly, the analyzed images/output may be sent to review stations 150, 160 anywhere in the world.

The image analysis system 120 performs the preprocessing, recognition, and/or post-processing of the images. Exemplary image acquisition systems 120 that may be used for this are described in U.S. Pat. No. 5,828,774 to Wang, and co-pending application Ser. No. 09/992/059, by Roehrig et al. entitled "A Method and Apparatus for an Improved Computer Aided Diagnosis System."

The HIS/RIS (hospital information system/radiology information system) system 170 is coupled to the image analysis system 120, either directly or through network 110. The HIS/RIS system 170 provides patient information, in one of a variety of formats. Patient information may include patient data identifying the patient, as well as patient historical data, providing relevant historical information. For one embodiment, the HIS/RIS system 170 may provide data in the HL7 format. Alternative formats may be used.

The images processed by image analysis system 120 may be stored within a patient record, in the DICOM format. Alternative standardized, non-standardized, or proprietary formats may be used to store the image data, with or without the patient information.

For one embodiment, copies of the processed images are stored in system archive 145, such that at a later time, the previous images may be retrieved. For one embodiment, auto-converter 140 converts the images to a DICOM format. For one embodiment, the auto-converter 140 further converts the image to a lower resolution image, which is stored. For one embodiment, the stored image does not include any tagging or other indicators added by image analysis system 120. For another embodiment, the owner of the system may set the preferences as to the images stored in system archive 145.

The images are displayed to a reviewer at review station 150. Review stations 150 may be directly coupled to image analysis system 120, or coupled through a network. Review stations 150 may be incorporated into a motorized viewer, as described in U.S. Pat. No. 5,917,292, to Marshall et al. Alternatively, a review station 150 may be an independent display. Such an independent display review station 150 is described in more detail below.

For one embodiment, the images may further be viewed at remote viewing stations 160. Remote viewing stations 160 may be conventional computer systems coupled to the network 110. For one embodiment, the remote viewing station 160 may be a handheld device. Remote viewing stations 160 permit a doctor in a remote location to review the images, and may be used to allow the patient or others to review the images remotely. Thus, for example, a radiologist at a central location may initially review and analyze the images, and annotate them. Then, the images, and notation—or a report generated based on the images and notation—is sent to a remote system where the doctor can review the data with the client.

The images, report, or other output may be sent to a printer 180. The printer 180, for one embodiment, may print to film, to permit conventional review of the enhanced images. For one embodiment, the printer 180 may print multiple images, for example, one set of original images, a set of enhanced images, and a set of enhanced images with markers indicating the abnormalities found by the image analysis system 120. The printer 180 may be coupled to the image analysis system 120 and/or the system archive 140 either directly or through network 110. As discussed above with respect to the review stations 150, 160, the printer 180 need not be in the same location as the image analysis system 120.

Of course, not all of these elements must be present in order to implement the present system. At its simplest, the system includes an image acquisition module 130A, an image analysis system 120, and a handheld device 160 that permits viewing of the images. These systems 120, 130A, 150 may be coupled directly, without the use of a network 110. At its most complex, the system may be a distributed system having image acquisition modules 130A, 130B at various remote locations, while a central archive 140 and one or more image analysis systems 120 are used to process the acquired images. Then, the images may be sent to various local or remote review stations 150, 160. Note that although the image analysis system 120 illustrated as once central device, it may be a distributed system.

Figure 2:
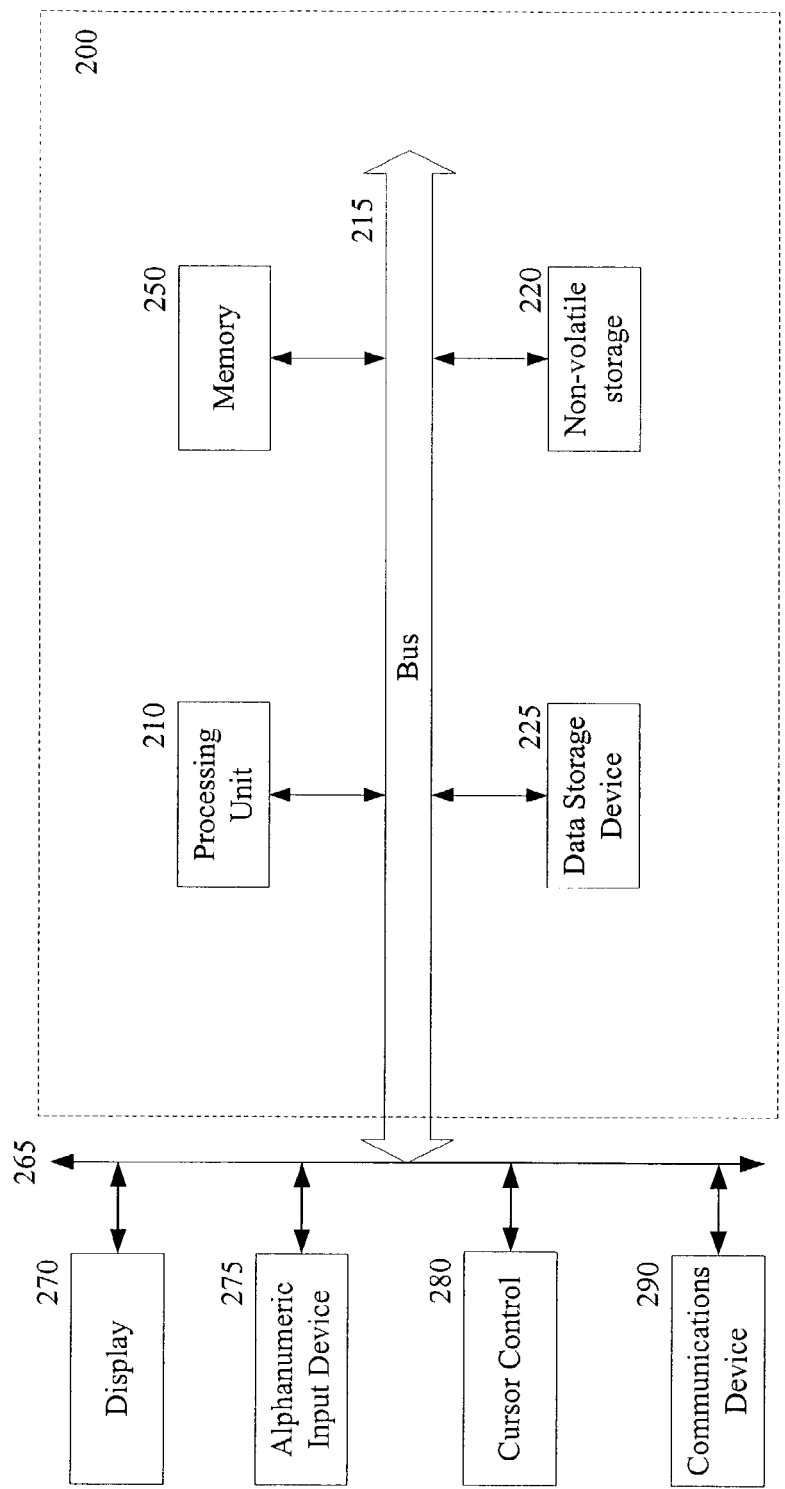
FIG. 2 is a block diagram of a computer system that may be used in conjunction with the present system.

FIG. 2 is one embodiment of computer system on which the present invention may be implemented. It will be apparent to those of ordinary skill in the art, however that other alternative systems of various system architectures may also be used.

The computer system illustrated in FIG. 2 includes a bus or other internal communication means 215 for communicating information, and a processor 210 coupled to the bus 215 for processing information. The system further comprises a random access memory (RAM) or other volatile storage device 250 (referred to as memory), coupled to bus 215 for storing information and instructions to be executed by processor 210. Main memory 250 also may be used for storing temporary variables or other intermediate information during execution of instructions by processor 210. The system also comprises a read only memory (ROM) and/or static storage device 220 coupled to bus 215 for storing static information and instructions for processor 210, and a data storage device 225 such as a magnetic disk or optical disk and its corresponding disk drive. Data storage device 225 is coupled to bus 215 for storing information and instructions.

The system may further be coupled to a display device 270, such as a cathode ray tube (CRT) or a liquid crystal display (LCD) coupled to bus 215 through bus 265 for displaying information to a computer user. An alphanumeric input device 275, including alphanumeric and other keys, may also be coupled to bus 215 through bus 265 for communicating information and command selections to processor 240. An additional user input device is cursor control device 280, such as a mouse, a trackball, stylus, or cursor direction keys coupled to bus 245 through bus 265 for communicating direction information and command selections to processor 210, and for controlling cursor movement on display device 270.

Another device that may optionally be coupled to computer system 200 is a communication device 290 for accessing other nodes of a distributed system via a network. The communication device 290 may include any of a number of commercially available networking peripheral devices such as those used for coupling to an Ethernet, token ring, Internet, or wide area network. Note that any or all of the components of this system illustrated in FIG. 2 and associated hardware may be used in various embodiments of the present invention.

For one embodiment, display 270, input device 275, and cursor control 280 may be combined into a single touch-screen. The touch screen display permits data entry using a touch sensitive screen.

It will be appreciated by those of ordinary skill in the art that any configuration of the system may be used for various purposes according to the particular implementation. The control logic or software implementing the present invention can be stored in main memory 220, mass storage device 225, or other storage medium locally or remotely accessible to processor 210. Other storage media may include floppy disks, memory cards, flash memory, or CD-ROM drives.

It will be apparent to those of ordinary skill in the art that the methods and processes described herein can be implemented as software stored in main memory 250 or read only memory 220 and executed by processor 210. This control logic or software may also be resident on an article of manufacture comprising a computer readable medium having computer readable program code embodied therein and being readable by the mass storage device 225 and for causing the processor 210 to operate in accordance with the methods and teachings herein.

The software of the present invention may also be embodied in a dedicated appliance containing a subset of the computer hardware components described above. For example, the dedicated appliance may be configured to contain only the bus 215, the processor 210, and memory 250 and/or 225, and a touch screen.

The device may also be configured to include a set of buttons or input signaling components with which a user may select from a set of available options. The dedicated appliance may also be configured to include an output apparatus such as a liquid crystal display (LCD) or display element matrix for displaying information to a user of the dedicated appliance. Conventional methods may be used to implement such a dedicated appliance. The implementation of the present invention for such a device would be apparent to one of ordinary skill in the art given the disclosure of the present invention as provided herein.

Figure 3:
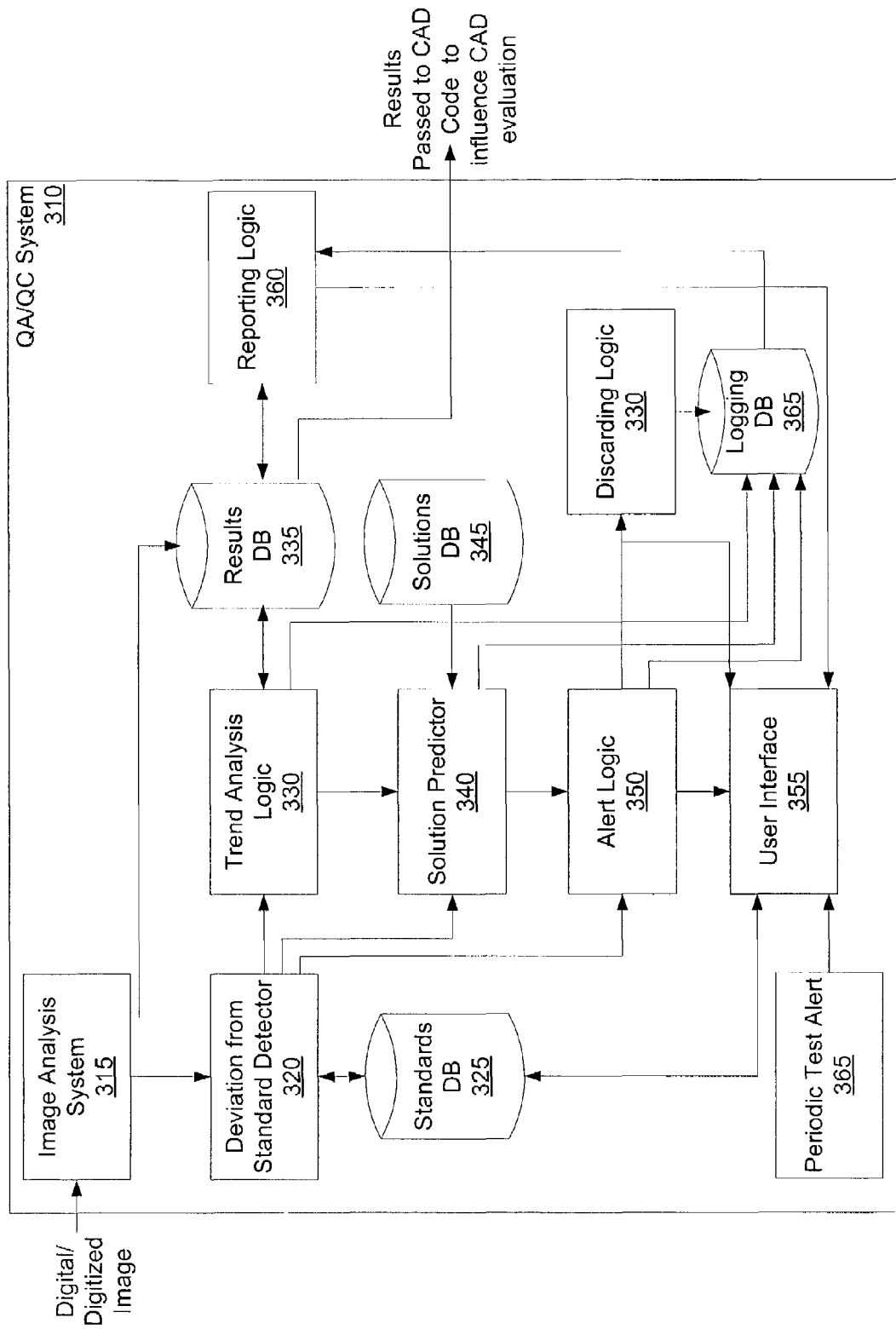
FIG. 3 is a diagram illustrating one embodiment of the quality control and quality assurance (QA/QC) system.

FIG. 3 is a block diagram of one embodiment of a quality evaluation system. The quality evaluation system 310 (or QA/QC system) receives a digital image. The image may be an image from a digital detector or a digitized film image. The image may be a standard medical image, which may be prepared for CAD analysis for the continuous QC analysis, or a special testing image for the periodic QA analysis. For the periodic QA testing, the periodic test alert 365 may be programmed to alert the user that the periodic test should be performed, and the test exposures should be taken.

The image is input to the image analysis system 315. The image analysis system 315 analyzes the image. The image may be a digital image from a digital detector. For another embodiment, the image may be a digitized image, originally obtained from a film, and digitized. A QC image may be any medical image, such as a mammogram, an X-ray, a CT scan, or any other type of medical image. The QA images are prescribed test exposure images, used to test the technologist's technique as well as the elements of the imaging system.

Deviation detector 320 compares the image to standards 325. As will be discussed in more detail below, the standards 325 may be international or national standards, such as the FDA standard prescribed for medical procedures in the United States. Alternatively and additionally, the standards may be variable standards defined by user, through user interface 355. The deviation detector 320 determines how much, if any, the current image deviates from the standards set up for the particular medical or testing image. The results of the deviation detector's 320 analysis are stored in results database 335.

The results of the analysis are passed to trend analysis logic 330. Trend analysis logic 330 uses historical results, from results database 335, to determine whether there are any negative trends. Negative trends are generally increasing deviations from a standard. The trend analysis logic 330 identifies any trends in the results. For one embodiment, the trends are recorded in results database 335 as well.

If the trend is negative—e.g. deviations are increasing—the trend analysis logic 330 passes the data to the solution predictor 340. The solution predictor uses solutions database 345 to attempt to identify likely causes of the negative trend. For one embodiment, deviation detector 320 further passes any detected deviations from the norm to solution predictor directly, if the deviation is sufficient to require a solution. In this way, trends are caught before they reach a problem stage, while problems are caught immediately.

If the deviation from the standard is sufficiently severe, e.g. above a certain threshold, the data is passed to alert logic 350. The alert logic 350 alerts the user that there is a significant problem that must be corrected. The alert may be visual, text based, auditory, or any other form or combination of forms. The alert logic 350 may also alert the user if the current image needs to be retaken. An image may need to be retaken because the patient moved, or there was some other problem that sufficiently impacts the image that it cannot be successfully analyzed.

For one embodiment, one or more of the systems including the deviation detector 320, trend analysis logic 330, solution predictor 340, and alert logic 350 log the results in logging database 365. The logging database 365 logs the results of the trend analysis, and solution predictor. For one embodiment, the user may enter the resolution of the problem as well, through user interface 355.

For one embodiment, if the image must be retaken, alert logic 350 passes the information to discarding logic 330. Discarding logic 330 then discards the image from the logging database 365. Otherwise, all results are logged in logging database 365. For one embodiment, even if an image must be retaken, it is stored in the logging database 365, and archived.

The user may request results either from results database 335 and/or from logging database 365. The reports created by reporting logic 360, for one embodiment comply with requirements, such as FDA reporting requirements. For one embodiment, the reporting logic 360 uses the PenRad Mammography Information, Reporting, Tracking System by PenRad Technologies of Minnesota. For one embodiment, the user may set the format and output preferences, and the reporting logic 360 can create reports focusing on results, technicians, hardware, overall performance, or any other characteristics that may be of interest.

Figure 4:
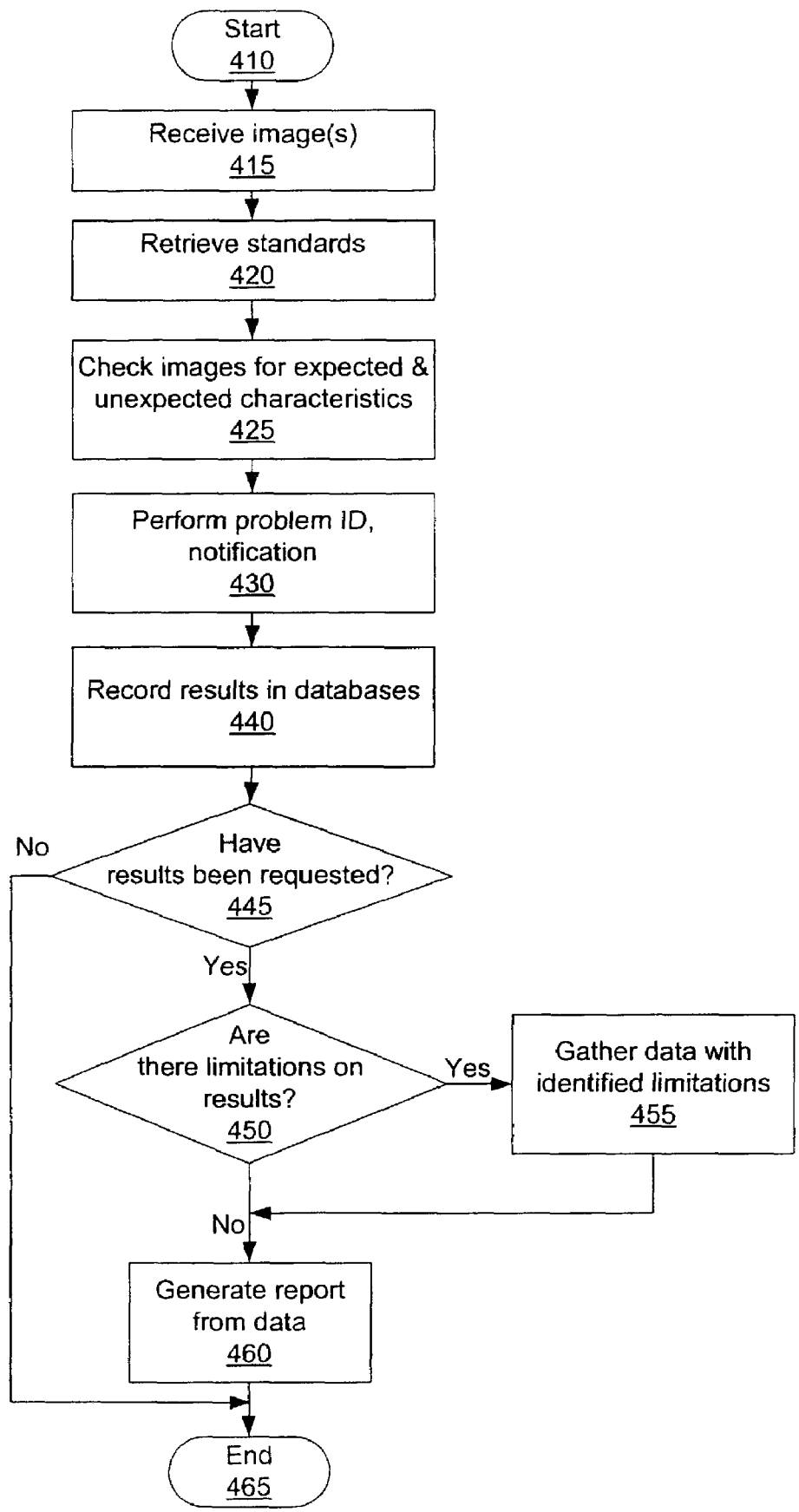
FIG. 4 is an overview flowchart of one embodiment of using the QA/QC system.

FIG. 4 is an overview flowchart of on embodiment of using the present quality evaluation system. The process starts at block 410. Note that this process applies both to continuous testing (QC) and periodic testing (QA). In general, QA is mandated by the FDA or similar regulatory agencies. The QC process makes sure the quality of the images is generally good. The QC process may be used to monitor particular technicians' performance, hardware performance, as well as overall effectiveness of the tests. At block 415, a digital image is received. The image may be digitally obtained, or digitized from a film-based image.

At block 420, the standards that apply to the image are retrieved. In general, for QC continuous testing, there are modality-specific and generic standards. For QA testing, most of the standards are prescribed by various regulatory agencies such as the FDA. FIG. 7 is a table showing some of the potential standards and deviations tested. FIG. 7 shows some mammogram specific tests, such as compression. However, in general, the tests described in FIG. 7 may be used as a basic set. The standard, for example, for "dirt on the screen" may be that dirt may be "no more than a grouping of three pixels." Alternatively, there may be an absolute rule that states that "any indication of dirt on the screen is a deviation from the standard." The actual details of such standards are described for example in Mammography Quality Standards Act (MQSA) of 1992.

At bock 425, the images are tested against the standards. For one embodiment, in addition for testing for unexpected characteristics such as dirt on the screen, fog, or motion blur, the system tests for expected characteristics. For example, for a mammogram an expected characteristic is that the pectoral muscle reaches from approximately the center of the top to approximately the center of the side of the image. The absence of such expected characteristics is also considered a failure to meet a standard.

At block 430, any problems are identified. As will be described below in more detail, the problems may be a failure to meet a minimum required standard, or a negative trend based on historical data. The process further notifies the technician if the deviation or is sufficiently severe to require immediate action. The immediate action may be retaking the image, adjusting the hardware, or making changes.

At block 440, the results are recorded in databases. For one embodiment, QA results are recorded in a preset format, as mandated by government standards. For one embodiment, the QC results are also recorded. This type of record provides full data for later review, for learning, training, retraining, and corrections.

At block 445, the process determines whether results have been requested. For one embodiment, the administrator may request reports. For one embodiment, a technician may create reports. If no results have been requested, the process continues to block 465, and ends. If a report has been requested, the process continues to block 450.

At block 450, the process determines whether the requested report has specified certain limitations. The report may request a certain date range, a certain technician, or any other quantifiable aspect of the reports. For one embodiment, the limitation may be to create a report in compliance with regulatory requirements. If limitations have been set, the process continues to block 455, and data is gathered with the identified limitations. The process then continues to block 460, and a report is generated. If no limitations are specified, the process continues directly to block 460, to generate a report. The format of the report, as discussed above, may be specified by the user. For one embodiment, the format complies with the reporting requirements for the FDA. For one embodiment, the report may further comply with regulation of other regulatory agencies, as appropriate.

Figure 5A:
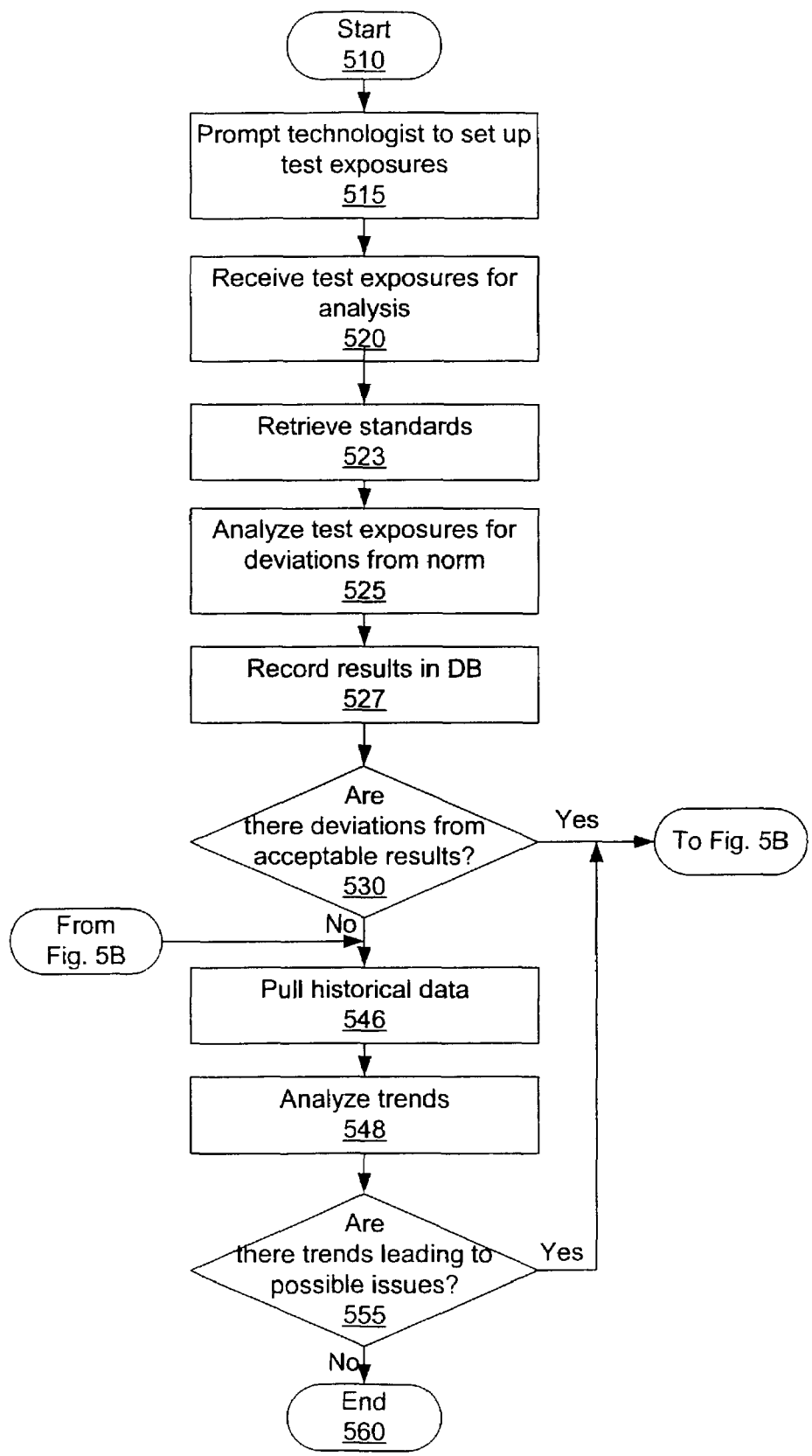
FIGS. 5A-B are flowcharts of one embodiment of using quality assurance (QA) periodic testing.
Figure 5B:
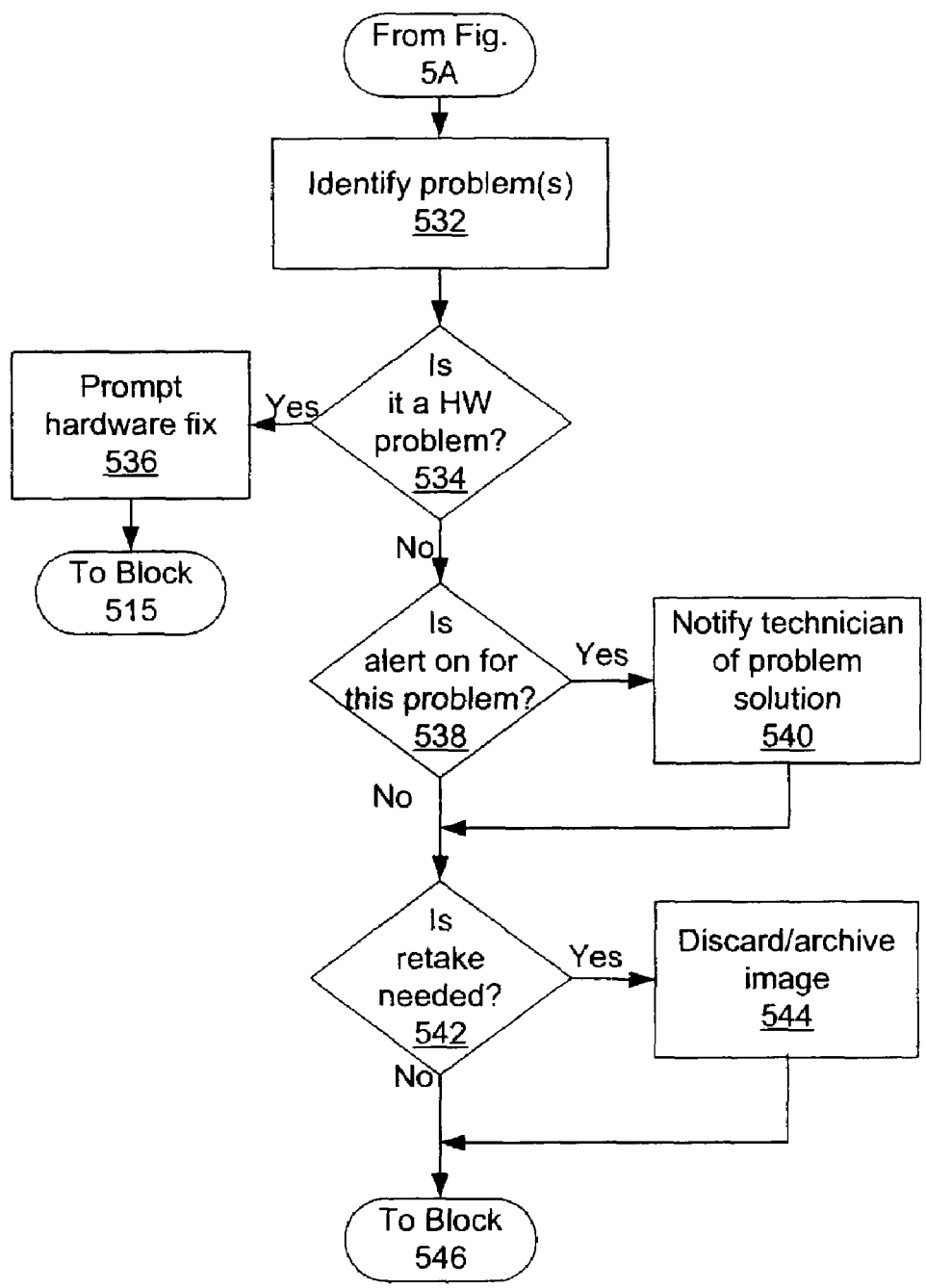

FIGS. 5A-B are flowcharts of one embodiment of using quality assurance, the periodic testing of the system. The process starts at block 510. At block 515, the technologist is prompted to set up the test exposures. In general, QC procedures require the exposure of various test images, and blank images to test the equipment and the process. At block 520, the test exposures are received for analysis. For one embodiment, in a film-based system, the technologist exposes the test exposures, develops them, digitizes them, and then activates the QC process. For one embodiment, in a digital test system, the technologist exposes the test images and activates the QC process.

At block 523, the standards are retrieved. As discussed above, the standards are based, for one embodiment, on government-mandated standards. For example, for mammograms, the FDA prescribes certain QA test procedures, and requires tracking of the results. The FDA further indicates what are acceptable response ranges or responses for the test. These standards, other applicable standards from other countries, and any variable standards set up by the user, are retrieved. As described below in more detail, the user may set up which standard or set of standards is used for this evaluation.

At block 525, the test exposures are analyzed to determine whether they deviate from the norm provided by the standards. For one embodiment, the norm may be a particular range, or a particular maximum or minimum value. For example, for the resolution test, the standard may be that the modulation transfer function (MTS) value is between 20 and 30 percent.

At block 527, the results of the tests are recorded in the database. For many government-mandated standards, the recording of the results is required. The database, for one embodiment, records in a format that can be used for compliance with such standards.

At block 530, the process determines whether there are any deviations from the acceptable results. If there are, the process continues to block 532, shown on FIG. 5B. Otherwise, the process continues to block 546.

At block 546, historical data is pulled from the results database.

At block 548, the process analyzes trends. Trend analysis determines the changes in the deviations from the norm over time.

At block 555, the process determines whether the trends are leading to possible issues. If there is a distinct trend, which appears to lead further from the standard, the process continues to FIG. 5B. If the process does not lead to possible issues, the process ends at block 560.

FIG. 5B is reached if there is a deviation from acceptable result, or if the trend is showing a consistent deviation. At block 532, the problem or problems are identified.

At block 534, the process determines whether it is a hardware problem. If the problem is a hardware problem, the process continues to block 536. At block 536, a hardware fix is prompted. In general, hardware problems—and these include problems with the hardware to take the image and the hardware to develop the image—must be remedied externally. The process then returns to block 515. In general, after a hardware problem is resolved, the testing images are retaken.

If it is not a hardware problem, the process continues to block 538. At block 538, the process determines whether there is an alert enabled for the problem that has been detected. In general, certain types of problems require alerts. The specific problems that require alerts may be set by the user. For one embodiment, certain problems or types of problems may require an alert, according to FDA or similar regulations. For one embodiment, the alert may be set to a different level than the problem detection. For example, certain levels of the problem may not require a specific notification of the technician. Thus, at this point, the process may determine whether the deviation/problem is sufficiently significant to require an alert.

If so, at block 540, the technician is notified. For one embodiment, in addition to presenting the problem, the process attempts to present a solution. The problem, once identified, is looked up in the solutions database. Possible solutions are identified, and presented to the user. For one embodiment, if possible the solutions that are not applicable—for example if other results indicate that the possible solution is not applicable. For example, if one of the other tests showed that a particular problem could not have caused the observed deviation, the solution for that problem is not presented.

The process then continues to block 542. If there was no alert for the problem, the process continues directly to block 542.

At block 542, the process determines whether a retake of the image is needed. If the problem is sufficiently severe to make the other aspects of the quality impossible or difficult to evaluate, or if the problem solution would significantly change the results of the tests, the process may determine that a retake is necessary. If so, at block 544, the image is discarded, and the process continues to block 546, on FIG. 5A. For one embodiment, instead of discarding the image, the image is archived at this point. This may be done for regulatory reasons, or for reasons of completeness.

In this manner, the test exposures are periodically evaluated, the results are logged, and possible solutions are suggested for any problems that are detected. Note that although this was described with respect to a particular image, for one embodiment, a set of images is used for this evaluation. Thus, for example, multiple images may be evaluated together to determine deviations, identify problems, and identify solutions to the problems. Furthermore, a subset or all of the images may be retaken, if appropriate.

Figure 6:
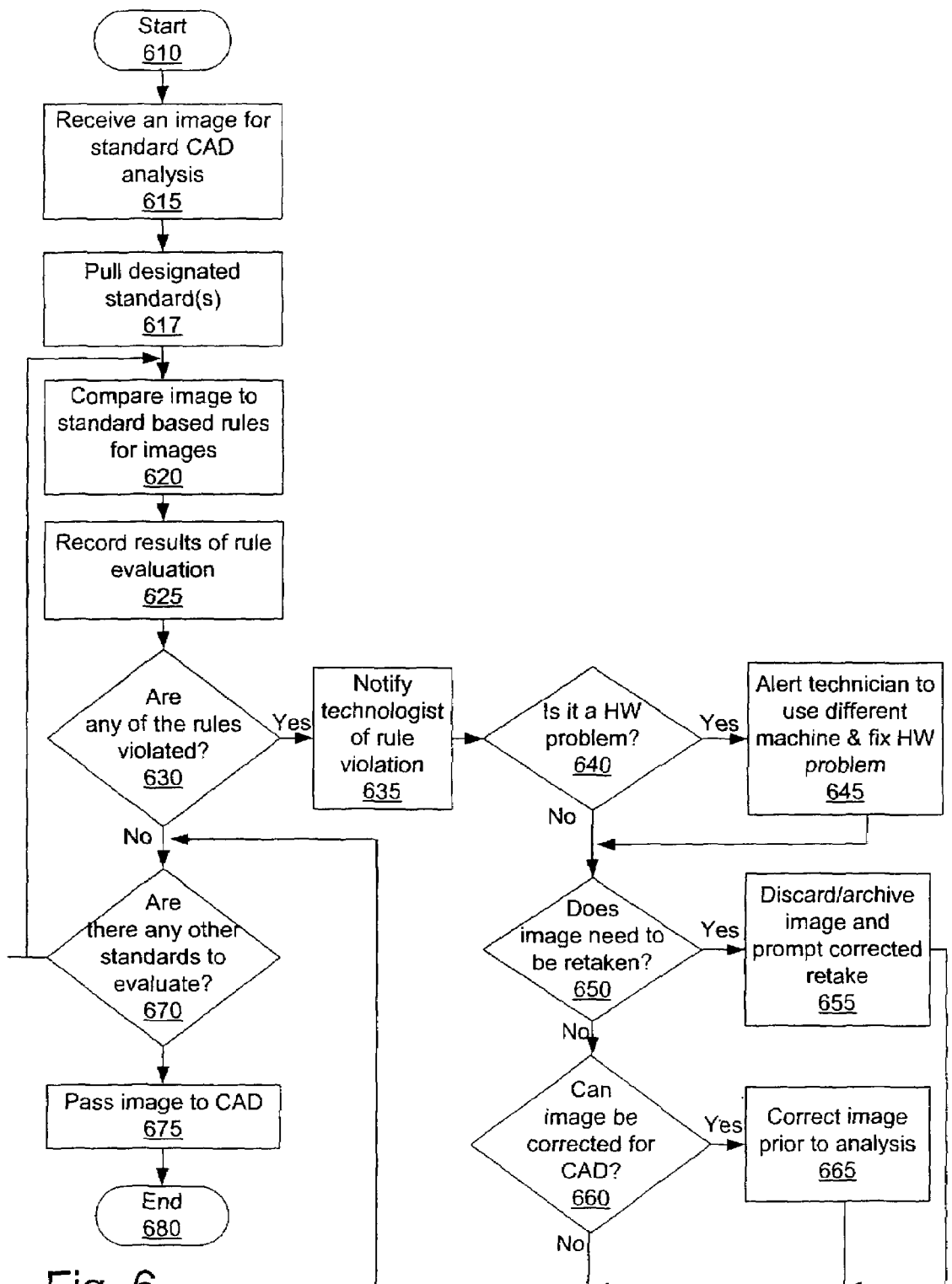
FIG. 6 is a flowchart of one embodiment of using quality control (QC) continuous testing.

FIG. 6 is a flowchart of one embodiment of using quality control. The process starts at block 610. For one embodiment, this process is automatically started for each new image that is received for processing. The processing, in this instance, may be digitizing and storing medical images and/or performing computer aided diagnosis/detection (CAD) on the images.

At block 615, an image is received. For one embodiment, the image is received for CAD analysis. For another embodiment, the image may be received for image correction, for archiving, or for another purpose.

At block 617, the designated standard(s) are pulled. As discussed above, the user may set one or more standards to evaluate the image. Each standard that is selected by the user is retrieved.

At block 620, the image is compared to the standard-based rules for the images. A standard specifies certain rules for an image. For example, the standard may specify that the color differential between the "empty" portion of the image and the "dense" portion of the image must be a certain depth. Similar types of standards may be applicable. FIG. 7 lists a set of exemplary standards. Note that this set of standards is not complete. One of skill in the art would be able to identify generic as well as process and modality dependent standards that would apply.

At block 625, the results of the rule evaluation are recorded. For one embodiment, all image evaluations are logged. This log may be used to evaluate technicians, hardware, and the overall system. The results may further be used to correct the CAD evaluation, if that is appropriate.

At block 630, the process determines whether any of the rules set by the standard have been violated. If so, the process continues to block 635. Otherwise, the process continues to block 670.

At block 670, the process determines whether there are any further standards to evaluate. If there are, the process returns to block 620, to compare the image to the rules based on the new standard. In this way, the process continues evaluating the image until all standards set up by the user have been evaluated. If there are no further standards to evaluate, at block 670, the process continues to block 675.

At block 675, the image is passed on for further processing. For one embodiment, the further processing may be CAD processing. For one embodiment, the CAD process described in U.S. Pat. No. 6,014,452 may be used to evaluate the image. For another embodiment, the processing may be archiving the image, or converting the image and associated data to a standard form such as DICOM. The process then ends at block 680.

If, at block 630, the process found that one or more of the rules have been violated, the process continued to block 635.

At block 635, the process notifies the technologist of the rule violation. For one embodiment, this notification may be visual, displaying on a screen. Alternatively, the notification may simply be a note in the file.

At block 640, the process determines whether the problem is a hardware (HW) problem. Hardware problems generally must be immediately corrected. If the problem is a hardware problem, the process continues to block 645. At block 645, the technician is alerted to the hardware problem. For one embodiment, the alert may include a notification to stop using the system until it is fixed. For one embodiment, if the hardware problem is not locally fixable, the system may further alert the hardware vendor to the problem. For one embodiment, if the present system is integrated with the hardware, the system may further shut down the hardware. The process then continues to block 650. If the problem is not a hardware problem, the process continues directly to block 650.

At block 650, the process determines whether the image needs to be retaken. If the problem is sufficiently severe, the image may not be of sufficient quality of analysis by a radiologist, or by the CAD process. For example, if sufficient motion blur is present, the image may not be analyzable. If the image must be retaken, the process continues to block 655. At block 655, the bad image is discarded and the technician is prompted to retake the image. For one embodiment, this process may take place immediately after a medical image is acquired. Thus, the patient would not need to return because the image was not of sufficiently good quality. For one embodiment, instead of discarding the bad image, the image may be archived. The process then continues to block 670.

If the image does not need to be retaken, at block 650, the process continues to block 660. At block 660, the process determines whether the image can be corrected. For one embodiment, for CAD processing, the image may be corrected, to compensate for certain types of problems. For example, if lack of contrast is an issue, the process described in U.S. patent application Ser. No. 10/079,327 may be used to correct the image. If the problem can be corrected for, the process continues to block 665, and the image is corrected. For one embodiment, the image correction may be used for the displayed image. For another embodiment, only the version of the image used by the CAD process is corrected, and the original unchanged image is presented to the radiologist for analysis.

The present process, as described above, permits each image to be analyzed as it is received. This improves the image processing, and alerts technicians to problems immediately. Furthermore, by providing immediate feedback, the present process ensures that a good quality image is obtained from the patient in a single session.

Figure 8A:
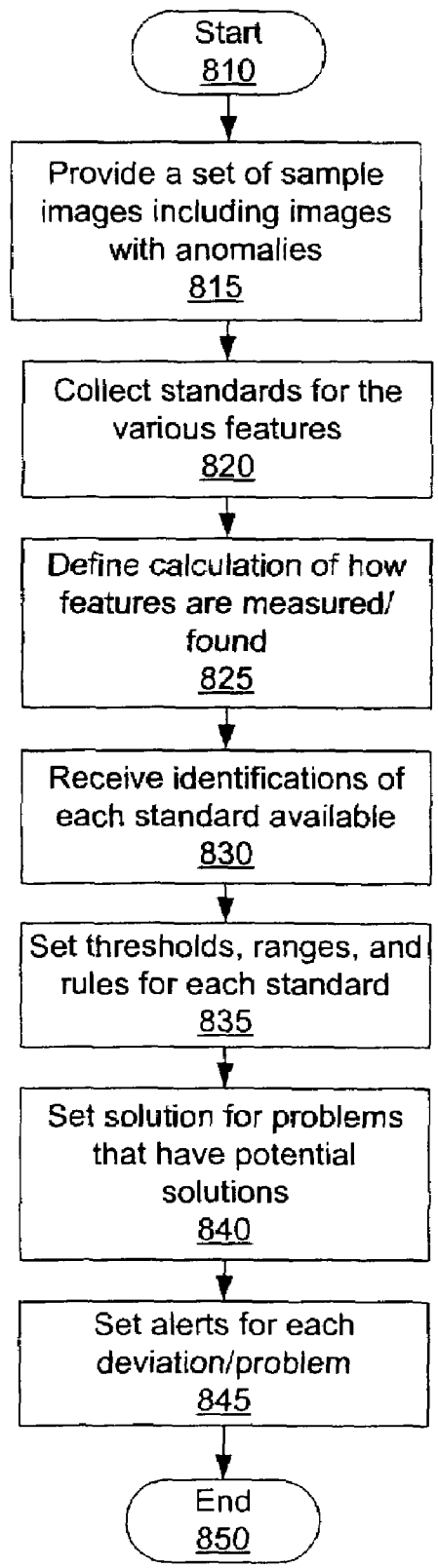
FIG. 8A is a flowchart of one embodiment of setting up the system to perform QA/QC procedures.

FIG. 8A is a flowchart of one embodiment of setting up the system to perform QA/QC procedures. The process starts at block 810. For one embodiment, this process is performed only once for each modality and imaging process. For another embodiment, this process may be regularly performed to refine settings.

At block 815, a set of sample images is provided, including images having anomalies. These images are used for training the present system.

At block 820, standards are collected for the various features. These standards are based, for one embodiment, on the sample images. For one embodiment, the standards may further be manually added. For example, the standard levels of contrast for an image are defined by the particular film being used.

At block 825, the calculations of how features are measured and found are defined. For example, the measurement of "placement" for a mammogram may be identified as having the pectoral muscle—an element having a particular characteristic density—in a particular location/zone. These calculations are known by those in the medical arts. Thus, the specifics of what defines "proper placement" for a mammogram, a CT scan, a chest X-ray, or another medical image are defined. Similarly, the characteristics that identify various anomalies and features—such as motion blur, dirt on the screen, fogging, etc. are identified. An exemplary list of characteristics that may be defined is included in FIG. 7.

At block 830, the system receives identification of the various available standards. For one embodiment, the standards may be regulatory standards, such as those promulgated by the Food and Drug Administration, or by the Health and Human Services division. For one embodiment, the standards may be standards promulgated by other countries. For one embodiment, at least a multiplicity of standards is entered into the system. For one embodiment, the standard for each country in which the device is made available is programmed into the system. For one embodiment, additional standards may be programmed in as well.

At block 835, the thresholds, ranges, and rules for each standard are set. Each standard may have different thresholds on what abnormalities cannot be present, and what features must be present. These thresholds, ranges, and rules are defined by each standard. For one embodiment, there may be a default value for any threshold, range, or rule that is not defined by the particular standard. For one embodiment, these thresholds, ranges, and rules include the settings that cause the alert to the technician, as well as the settings that are simply recorded as deviations from the expected. For one embodiment, these settings further include the trends that are considered a problem.

At block 840, solutions are set for the problems that have potential solutions. Most of the problems that may be detected in an image have solutions. For example, for dirt on the screen, the solution is to clean the screen. For faulty positioning, repositioning the patient is the simple solution. In general, for each defined problem there are one or more possible solutions. There may be some problems, such as lack of contrast, which may not have a single solution. Rather, a set of possible solutions would need to be explored to identify the actual problem and its solution.

At block 845, the alerts are set for each significant deviation/problem. As discussed above, these alerts may be set based on recognized standards, such as the standards provided by the FDA. For another embodiment, deviations of a certain level, e.g. more than 5% from norm, may be considered sufficient for an alert. The alerts are set at this point. The process then ends at block 850.

Figure 8B:
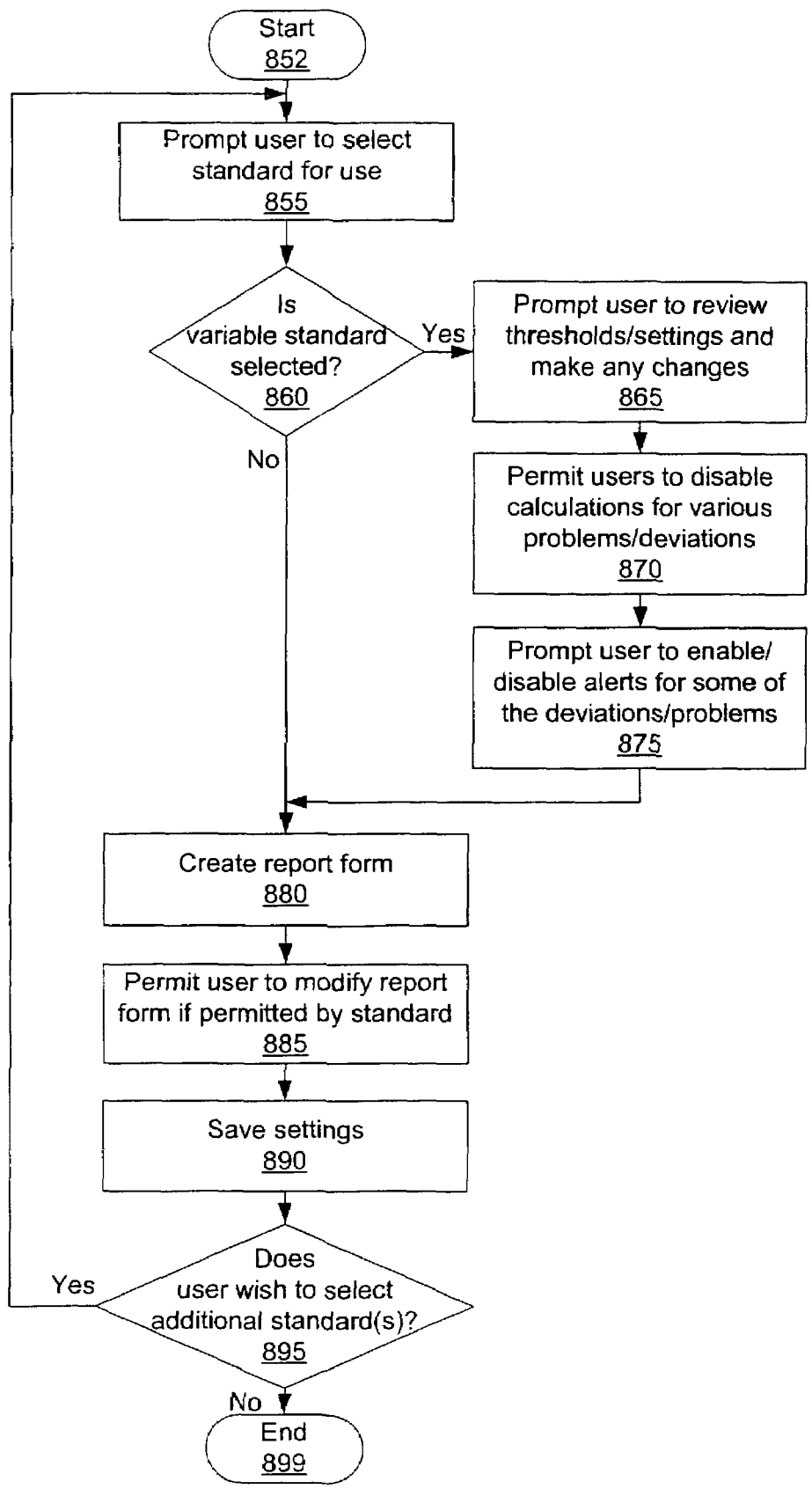
FIG. 8B is a flowchart of one embodiment of setting up the system to perform personalized QA/QC procedures.

FIG. 8B is a flowchart of one embodiment of setting up the system to perform QA/QC procedures. The process starts at block 852. This process customizes the device for the particular standards and preferences that the hospital or other facility wishes to use. In general, this type of setting-up is performed once when the first device is initially installed in the facility. For one embodiment, these settings may be transferred from device to device within a facility. For one embodiment, this type of programming may be transferred via a diskette, CD, network connection, or through some other means. Thus, a single facility that has multiple analysis systems only would program the system once.

At block 855, the user is prompted to select a standard to use for evaluating images. For one embodiment, the standard may be chosen from among the preset standards discussed above, or a variable standard set up by the user.

At block 860, the process determines if a variable standard has been selected. If one of the predefined standards is selected, the process continues to block 880. Otherwise, the process continues to block 865. At block 865, the user is prompted to review the thresholds and settings of the system. For one embodiment, these are the "default" settings discussed above, set at the factory. The user is permitted to make changes to these thresholds and settings.

At block 870, the user is permitted to disable calculations for various problems and deviations. For example, the facility may not wish to track, or may have no need to track "dosage" for example in a clinical setting where dosage is not adjusted by a technician, but is automatically calculated.

At block 875, the user is prompted to enable and disable alerts for the various deviations. The user may change the levels of deviation/problem that causes an alert. For one embodiment, the format of the alert may also be changed. For example, an alert may range from a notation in the file to a visual and auditory alert for the technician actually taking the medical image. The process then continues to block 880.

At block 880, the process creates a report form appropriate for the standard. At block 885, the user is permitted to alter the report form, if such alterations are permissible by the standard. For example, the FDA radiology standards have particular reports that must be presented to inspectors. The formats of those reports are set by the FDA. Thus, those report forms may not be changed by the user, if the user has selected the FDA standard.

At block 890, the settings are saved.

At block 895, the user is permitted to select an additional standard to use for evaluating the medical image. If an additional standard is selected, the process returns to block 855, to prompt the user to select a standard. If no additional standards are selected, the process ends at block 899.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method for quality control in radiological image acquisition, comprising:
   receiving a radiological image of a patient acquired using at least one piece of radiological equipment at least partially controlled by a technologist, the patient being controlled by the technologies relative to the radiological equipment in acquiring said radiological image;
   processing the radiological image by computer to test the radiological image to determine if the radiological image meets a preselected standard relating to at least one of: technologist control of the patient relative to the radiological equipment during the image acquisition and technologist preparation of the radiological equipment for the image acquisition, wherein said preselected standard relating to technologist control of the patient relative to the radiological equipment during the image acquisition relates to one of (a) proper placement of anatomical part of the patient relative to a detector of the radiological equipment, and (b) controlling movement of the anatomical part of the patient relative to the detector during image acquisition; and
   recording the results of the testing in a manner that associates said results with said technologist for facilitating evaluation of a performance of said technologist.

2. The method of claim 1, wherein the radiological image is destined for CAD processing to identify anatomical abnormalities therein subsequent to said testing against said preselected standard.

3. The method of claim 2, further comprising:
correcting the results based on the results of the testing.

4. The method of claim 2, further comprising:
passing the radiological image and the results to a CAD processing unit, wherein the results are used by the CAD processing unit to influence the CAD processing of the radiological image.

5. The method of claim 1, wherein recording the results comprises:
recording the results in a statistical database.

6. The method of claim 5, further comprising:
generating statistics on the radiological equipment based on the results.

7. The method of claim 6, wherein the statistics produce legally mandated reports, for purposes of compliance with legal requirements.

8. The method of claim 5, further comprising:
analyzing a plurality of results over time, to identify a trend in the results; and
recording the trend.

9. The method of claim 1, further comprising:
alerting the technologist if the results of the testing fail to meet a particular threshold.

10. The method of claim 9, wherein said processing is performed sufficiently close in time to the acquisition of the radiological image such that, upon said alerting the technician, the radiological image may be re-acquired prior to a departure of the patient from a location of the radiological equipment.

11. The method of claim 1, wherein said radiological equipment is mammography equipment, wherein said anatomical part is a breast, wherein said preselected standard for proper placement relates to one of (a1) pectoral muscle position relative to the detector and (a2) breast compression against the detector, and wherein said preselected standard for controlling movement relates to motion blur in the radiological image.

12. The method of claim 11, wherein said preselected standard relating to technologist preparation of the radiological equipment relates to an amount of dirt on a screen of the detector.

* * * * *